United States Patent [19]

Birkmayer

[11] Patent Number: 5,019,561

[45] Date of Patent: * May 28, 1991

[54] TREATMENT OF PARKINSON'S DISEASE WITH NADPH

[76] Inventor: Jorg Birkmayer, Schwarzspanierstrasse 15, A-1090 Vienna, Austria

[*] Notice: The portion of the term of this patent subsequent to Nov. 13, 2007 has been disclaimed.

[21] Appl. No.: 351,345

[22] Filed: May 15, 1989

[30] Foreign Application Priority Data

Jun. 3, 1988 [AT] Austria ................................. 1454/88

[51] Int. Cl.$^5$ .................. A61K 31/455; A61K 31/70; C07H 19/207
[52] U.S. Cl. .................................... 514/52; 424/94.1; 424/94.4
[58] Field of Search ................. 424/94.1, 94.4; 514/52

[56] References Cited

U.S. PATENT DOCUMENTS

| 3,266,989 | 8/1966 | O'Hollaren | 536/28 |
| 3,326,756 | 6/1967 | O'Hollaren | 424/94.1 |
| 3,341,412 | 9/1967 | O'Hollaren et al. | 424/94.1 |

FOREIGN PATENT DOCUMENTS

3542309A1 7/1987 Fed. Rep. of Germany.

OTHER PUBLICATIONS

Jung et al. (1989) Archives of Pharmacology vol. 339, pp. 424–432.
Nichol et al. (1985) Ann. Rev. Biochem. vol. 54, pp. 729 and 735.
White et al. (1973) *Principles of Biochemistry* Fifth Edition, McGraw-Hill Book Co., New York, p. 218.
The Merck Index, Ninth Edition No. 6172.

*Primary Examiner*—Johnnie R. Brown
*Assistant Examiner*—Gary L. Kunz
*Attorney, Agent, or Firm*—Nixon & Vanderhye

[57] ABSTRACT

Use of the enzyme cofactor NADPH or a salt thereof for the preparation of a medicament suitable for treating Parkinsonism.

4 Claims, No Drawings

TREATMENT OF PARKINSON'S DISEASE WITH NADPH

The invention relates to the use of the enzyme cofactor NADPH or a salt thereof for the preparation of a medicament suitable for treating Parkinsonism as well as a medicament for the treatment of Parkinsonism containing the enzyme cofactor NADPH or a salt thereof and a process for its preparation.

Parkinson's disease is caused by defective dopaminergic neurotransmission in the basal ganglia, generally as a result of an increasing decline in the dopaminergic neurons first in the substantia nigra and, as the disease progresses, also in other regions. In advanced cases an increasing noradrenaline deficiency (e.g. in the locus caeruleus) can also be ascertained. A very clear drop in tyrosine-hydroxylase activity, which interestingly is also sharply reduced in other systems and organs (e.g. in the suprarenal medulla) is also found in early stages of the disease (see Table 3 from Birkmayer and Riederer, Die Parkinson-Krankheit (Parkinson's Disease), 2nd Edition, page 34, Springer Verlag Vienna, 1985).

TABLE 3
Tyrosine hydroxylase in various regions of the brain in Parkinson's disease

| Brain region | | Controls | Parkinson's disease |
|---|---|---|---|
| N. caudatus | (15) | 27.8 ± 2.3 | 3.5 ± 1.0 (6)* |
| Putamen | (5) | 16.2 ± 5.9 | 1.2 ± 0.4 (6)* |
| S. nigra | (4) | 19.4 ± 6.2 | 4.9 ± 1.8 (4)* |
| L. caeruleus | (4) | 3.3 ± 0.1 | 2.0 ± 0.6 (2) |
| N. ruber | (5) | 5.7 ± 1.9 | 2.1 ± 1.4 (3) |
| Raphe + R.F. | (4) | 0.9 ± 0.6 | 1.5 ± 0.4 (5) |
| Hypothalamus | (5) | 3.1 ± 1.0 | 1.5 ± 0.3 (3) |
| C. mamillare | (5) | 0.6 ± 0.4 | 0.5 ± 0.9 (2) |
| N. accumbens | (5) | 2.0 ± 0.7 | 2.7 ± 2.2 (3) |
| Suprarenal (Medulla) | (5) | 186.2 ± 5.5 | 49.7 ± 12.4 (4)* |

Number of patients in brackets
Average ± sem (nmol dopa/g-tissue.hour)
*p < 0.01

In conventional therapies the deficient or diminished dopaminergic activity is replaced by the dopamine preliminary stage L-dopa. As this effect diminishes, the L-dopa effect can be increased again by specifically inhibiting the enzyme MAO-B which breaks down dopamine.

Although the life expectancy of the patients was improved, after years of use these treatments often resulted, however, in severe and unforeseeable variations in mobility (fluctuations, on-off phenomenon) which seriously affect the quality of life of the patients. These variations can be partially avoided or at least diminished by the timely use of postsynaptic agonists such as Lisuride.

According to Birkmayer and Riederer, a temporary enzyme depletion of tyrosine-hydroxylase underlies the sudden restriction in mobility (Birkmayer and Riederer, Die Parkinson-Krankheit (Parkinson's Disease) 2nd Edition, page 81, Springer Verlag Vienna, 1985). In fact, increased loading on tyrosine-hydroxylase can also be postulated biochemically by some of the standard therapies.

It is to be assumed that under normal conditions this key enzyme of dopamine (and noradrenaline) synthesis is sufficiently induced and provided with cofactors. In Parkinsonism, however, an error in programming of the tyrosine-hydroxylase synthesis can be a causative factor.

Clinical tests have surprisingly shown that a dramatic improvement in motoricity is achieved even in patients with advanced Parkinsonism and severe variations in mobility, by administering the enzyme cofactor NADPH (nicotinamide adenine phosphate dinucleotide in reduced form). Important in this case was the use of the reduced form since NADP proved ineffective to a large extent.

The clinical results are illustrated in the following table by the example of two patients with Parkinson's disease.

CASE 1

Duration of illness—3 years; age—43 without therapy

First examined on May 11, 1987; pain in both shoulders for one year and trembling of left hand; dragging of left foot. Objective finding: left foot dragged along when walking. Lifting left arm up until fully extended not possible. Speech slightly dysarthric. Associated movements on the left side missing.

Diagnosis: hemiparkinsonism, disability 20.

Therapy: Madopar (R) 125 (=L-dopa+Benserazide) three times daily Jumex (R) (=dePrenyl), twice half a tablet.

Checked: Nov. 18, 1987. Premature fatigue, rigidity of the left side of the body, walks with short steps, left foot drags.

Disability 40, evenings off-phase of 2-3 hours, stiffness of the left side.

NADPH 25 mg once per week, short-term improvement.

Checked on Mar. 23, 1988: hemiparkinsonism on the left side, disability 50, off-phase 2-3 hours daily.

Therapy: NADPH 25 mg, twice weekly

Checked: May 10, 1988. Completely normal mobility, no rigidity or tremor, NADPH, intramuscular, 25 mg, once per week guarantees 3 to 5 days of normal mobility. As the effect diminishes one Madopar (R) 125 daily suffices. Continuation of therapy with NADPH without Madopar (R).

Disability 0, completely normal mobility, evenings tired, movements slowed down.

CASE 2

Duration of illness—3 years; age—58

Cranial trauma while skiing; unconscious for 4 hours (Feb. 13, 1985). After three years, drags right foot, speaks quietly, jumping impossible.

Diagnosis: posttraumatic Parkinsonism

Therapy: Madopar (R) 200/50 (=L-dopa+Benserazide) three times half a tablet daily, Jumex (R) (=deprenyl) once daily.

Disability 30 (Feb. 13, 1985)

Jan. 29, 1986 —disability 15

Condition improved, continuation of therapy

Checked: Feb. 23, 1988

Has been aware for one year that his disease is progressing. Takes small steps when walking, shuffles, lifting upwards not possible, unable to jump on ground, speech quiet and poorly articulated.

RR 110/80, standing 90/70

Therapy: Madopar (R) 125/6 (=L-dopa+Benserazide) daily, Jumex twice daily.

Disability 40.

Apr. 14, 1988 —disability 40

Therapy: NADPH 25 mg twice weekly, intramuscular

Disability after one week 20 (at the start of the effect short-term hyperkinesia. Interruption of Madopar (R) treatment, after three weeks disability 15 (slight weakness during longer walks). The duration of the effect is extended following continuation of these injections; takes 2 Madopar (R) 125 (=L-dopa+Benserazide) daily and NADPH 25 mg twice weekly.

The patients' data show that taking NADPH or a salt thereof clearly improves the disability. This was established both in the on and in the off-phase and is achieved both when administering standard preparations simultaneously as well as without simultaneous administration of known parkinsonian remedies. A shortening of the off-phase is also achieved with the medication according to the invention.

For use according to the invention the co-enzyme NADPH or its physiologically compatible salt can be manufactured in the usual manner with pharmaceutically acceptable auxiliaries and carrier materials. If necessary, NADPH can also be used in combination with other active ingredients, for example postsynaptic dopamine agonists such as Lisuride or Amorphine. The simultaneous administration of monosubstituted organoselenium compounds, such as selenoamino acids, selenoproteins and selenopolypeptides, proved particularly effective, whereby synergism was ascertained, its effect surpassing the isolated administration of monosubstituted organoselenium compounds and NADPH.

For use as a medicament NADPH can be worked in in the usual Galenic forms of preparation for oral, parenteral (such as intravenous or subcutaneous) or sublingual application. The preparations can be in solid form as tablets, capsules, dragees or in liquid form as solutions, suspensions, sprays or emulsions as well as preparations with a delayed active ingredient. To improve the motoricity in patients with Parkinson's disease the single dose in parenteral application amounts to between 5 to 500 mg, preferably between 25 to 100 mg, and the daily dose amounts to between 5 to 1500 mg, preferably 25 to 300 mg.

The oral doses can be in the same range as the quantities of active ingredient to be applied parenterally or possibly 1000% higher.

If the co-enzyme NADPH is present in the form of its physiologically compatible salt, then all known acidic and basic salt formersare suitable, as well as organic and inorganic acids such as, for example, hydrochloric acid, sulfuric acid, citric acid, maleic acid and alkali and alkaline earth metal hydroxides and salts.

I claim:

1. A method of treating Parkinsonism, said method comprising the step of administering to a patient suffering from Parkinsonism an effective amount of the enzyme cofactor NADPH or a physiologically compatible salt thereof.

2. A method according to claim 1, wherein said enzyme cofactor NADPH or salt thereof is administered in association with a monosubstituted organoselenium compound.

3. A method according to claim 2, wherein said monosubstituted organoselenium compound is selected from the group consisting of a selenoamino acid, a selenoprotein and a selenopolypeptide.

4. A method according to claim 3, wherein said monosubstituted organoselenium compound is selected from the group consisting of selenomethionine, selenocysteine and selenotyrosine.

* * * * *